(12) United States Patent
Lewis

(10) Patent No.: US 11,517,467 B1
(45) Date of Patent: Dec. 6, 2022

(54) RESTORATIVE APPARATUS WITH METHOD FOR MALE TISSUE GROWTH

(71) Applicant: Jeffrey Lewis, Saint Joseph, LA (US)

(72) Inventor: Jeffrey Lewis, Saint Joseph, LA (US)

( * ) Notice: Subject to any disclaimer, the term of this patent is extended or adjusted under 35 U.S.C. 154(b) by 0 days.

(21) Appl. No.: 17/529,221

(22) Filed: Nov. 17, 2021

(51) Int. Cl.
*A61F 5/41* (2006.01)
*A61H 23/02* (2006.01)

(52) U.S. Cl.
CPC .............. *A61F 5/41* (2013.01); *A61H 23/02* (2013.01); *A61F 2005/417* (2013.01)

(58) Field of Classification Search
CPC ...... A61H 19/32; A61H 9/0057; A61H 19/30; A61H 2201/165; A61H 2201/5005; A61H 9/0007; A61H 19/00; A61H 2201/501; A61H 19/50; A61F 5/41; A61F 2005/412; A61F 2005/411; A61B 10/0058
USPC ..................................................... 600/38–40
See application file for complete search history.

(56) References Cited

U.S. PATENT DOCUMENTS

| 9,226,872 | B2 | 1/2016 | Pletnev |
| 10,646,399 | B2 | 5/2020 | Gordon |
| 2013/0018221 | A1 | 1/2013 | Ball |
| 2017/0224522 | A1 | 8/2017 | Irias |

FOREIGN PATENT DOCUMENTS

| CN | 211461787 U | 9/2020 |
| WO | WO2013178223 A2 | 12/2013 |

OTHER PUBLICATIONS

Muir,Kiel,Rubin, Safety and severity of accelerations delivered from whole body vibration exercise devices to standing adults, J Sci Med Sport, Nov. 2014, Fig.2.

*Primary Examiner* — Christine H Matthews
(74) *Attorney, Agent, or Firm* — Kelsey Stout Intellectual Property

(57) ABSTRACT

An apparatus allows a method for encouraging tissue growth in the penis and strengthening male urinary continence. An activation module encompassing a vacuum chamber is operatively connected with a vacuum pump and a vibration motor. A control module directs the operations of the vacuum pump and vibration module such that vacuum and vibration are applied to a user's penis in the vacuum chamber. Proper order of application of intervals of vacuum and vibration over multiple cycles characterizes performing the methods of the invention. Applying appropriate levels of vacuum and vibration over cycles and intervals within cycles also characterizes the invention.

29 Claims, 15 Drawing Sheets

RESTORATIVE APPARATUS WITH METHOD FOR MALE TISSUE GROWTH

FIELD OF THE INVENTION

The invention disclosure relates an apparatus and methods for encouraging regrowth or repair of penile tissue after surgery or injury.

BACKGROUND

Some types of urologic surgery or injury to the genitals can cause, as a side effect, a loss of penile mass. Many approaches have been tried to produce growth or regrowth of penile tissue mass, or what is commonly known as male enhancement. Attempts at producing male enhancement have taken four types of approaches.

Pills, creams and lotions are widely marketed and sold. However, they have no direct power to create penile tissue growth. There is no pharmaceutical means of directing a drug or compound to grow a specific area of the body that is similar tissue-wise to other areas. Products that grow hair, for example, are designed to act specifically on very unique cells. Despite the ineffectiveness of these products they still sell because they are easy to use, and men want to believe they can work.

Traction devices attach to the end of the penis and apply a steady tension for periods of up to many hours a day. These devices could be theorized to work because, as cells naturally die and are replaced, the dead cells will no longer hold adjacent cells as tightly and the replacement cells will adapt to the stretched configuration of the local cells. Conclusive studies indicating that this is effective in the long term are hard to find.

Traction devices are undesirable for at least three reasons. The first is that the penis is difficult to hold tight enough for long periods of traction without dangerously and painfully shutting off the blood supply. The second reason is that the traction devices must be worn for many hours a day to see any results. The third reason is that any length increase takes so long to develop that users give up.

There is a surgery to lengthen the penis. However it only lengthens it in the flaccid state; therefore it appears larger without being erect, but erections are no longer than before surgery. This surgery has three drawbacks.

First, surgery provides no functional increase in length. The surgically altered penis might become erect, but it will not stick out from the body. This means the penis must be manually directed during any sexual activity and an erection can appear to be a flaccid penis. Second are the surgical risks, including normal surgical risks such as infections but also including the risk of erectile dysfunction and loss of sensation. The third drawback is excessive cost.

Vacuum devices include a chamber to insert the penis along with a pump of some sort. The chamber is placed against the groin, often with a soft gasket to help seal the chamber to the groin. Most of the pumps are either hand powered or battery powered. The user slides the chamber over the penis, and then pumps until the desired vacuum is reached, whereupon the vacuum is held as long as the user chooses to leave it.

Vacuum devices are claimed to work; however, the medical community is generally unanimous that they have no lasting effects. The only medically approved use of vacuum devices is to create an erection suitable for penetration, often with the aid of an O-ring that is applied to the base of the penis once it is fully inflated via vacuum.

Vacuum devices fail for both usage and physiological problems. They are uncomfortable, especially at the vacuum levels required to generate the most stretch. Human skin is not particularly suited for exposure to applied vacuum. Blood is drawn into the area under the skin which is soon painful at higher vacuums and eventually painful at lesser vacuums. Whether or not vacuum can lead to real tissue growth, the level of vacuum required cannot be applied for long enough durations without unacceptable pain.

What is sought, then, is a means of inducing long-lasting growth or regrowth of penile tissue.

Inducing Tissue Growth

The stretching that vacuum devices create is not enough to permanently stretch the tissues. The cells of pliable tissue can be imagined as a set of connected spheres. When a tension is applied the cells can then be imagined as taking on an elliptical shape, with all of the cell-to-cell bonds remaining intact. This elliptical distortion can remain as long as the tension remains. However, release of the tension allows the cells to gradually return their spherical shape, free of any growth from the stretch.

Increase in tissue mass can occur through one of three methods. Enlargement of existing cells occurs in, for example, fat cells but not in penile tissue cells. Accumulation of additional tissue, such as scar tissue, collagen, from wound healing is not desirable for this purpose.

Instead, it is expected that the best method of inducing penile tissue regrowth is to cause micro-tears. A simplified understanding is that micro-tears are caused by exceeding the bond strength between adjoining cells, so as to allow new cells to be grown in between.

As explained above, direction tension cannot make this work. Various adjustments and strategies of applying and limiting the vacuum levels were tried but also did not work. Using water instead of air as the means of applying vacuum does not work.

SUMMARY OF THE INVENTION

When vacuum tension is applied to the penis, two things happen as it stretches to its natural length. First it fills with blood. Then the cells stretch into the elliptical model. Once the cells have become elliptical, they can withstand the strain indefinitely.

Testing indicated that what causes this strained, but withstanding, tissue to allow micro-tears at the most strained points is applying vibration. A mild vibration did not cause the micro-tears because the elliptical cells could simply stretch and relax the tiny bit required to move with the vibration and withstand the strain. Applying vibration before the tissue was fully tensioned by vacuum was also ineffective. What works is to fully tension the tissue with vacuum, and then apply vibration.

The invention applies a powerful vibration to the chamber tensioning the user's penis in vacuum for an interval of vacuum tensioning, an interval of tensioning with vibration, and a recovery interval of reduced-vacuum recovery. Multiple cycles of said intervals are controlled for interval duration, vacuum level and vibration intensity.

Using the invention involves sliding a vacuum chamber of an activation module over the penis and making it seal against the body. A button press starts the cycling process. The preferred process is 40 cycles of the following steps:

Vacuum is applied to the penis for the tensioning interval. The amount of vacuum is specific to the cycle number within the session. The first cycle begins at 20% vacuum.

Vibration is applied to the penis in activation module for a vibration interval. This conjunction of vacuum and vibration is held for approximately 10 seconds.

Vibration is halted and the vacuum is reduced to a very low level to allow time without any vacuum stress. The vacuum is not fully relieved so that the chamber maintains its seal on the body. This recovery interval is maintained for five seconds.

The process repeats for another of up to 40 cycles. Vacuum level for the tensioning interval is increased by 4% per cycle. The highest vacuum applied for any cycle is 17 in Hg, or 56.8%.

This increase per cycle can be limited by a user input via a control module's touch screen. The user selects a target vacuum where the increase stops. The user can also select number of cycles.

The length of the penis in the chamber is determined electronically using an ultrasonic sensor inside the end of the activation module. Using the ultrasonic sensor, it can be determined when the penis has reached ultimate length via vacuum tensioning and further length via vacuum in conjunction with vibration. Progress data for each cycle can be thereby recorded.

Vacuum is applied to the activation module via a vacuum pump, and vibration is applied via a vibration motor mounted to the activation module. Electrical components are controlled by an electronic control module capable of receiving user input via a touchscreen.

Using the apparatus with these steps has achieved measurable tissue growth. And, since effectiveness does not rely on excessive vacuum levels, discomfort is mild.

Thus, we see that the apparatus of the invention allows a method for encouraging tissue growth in the penis and penile blood flow, and, potentially, strengthening male urinary continence. It was found that the level of vacuum used by the invention can act as resistance for exercise. This exercise resistance affords the user opportunity to conveniently practice pelvic floor muscle exercise, further improving recovery from pelvic surgery or injury. Movement of the pelvic muscles can be sensed and measured using sensors of the apparatus, improving the user's confidence in what is otherwise an awkward exercise. This facilitated pelvic floor exercise is expected to reduce urinary incontinence following pelvic surgery.

DETAILED DESCRIPTION

Figure 1:
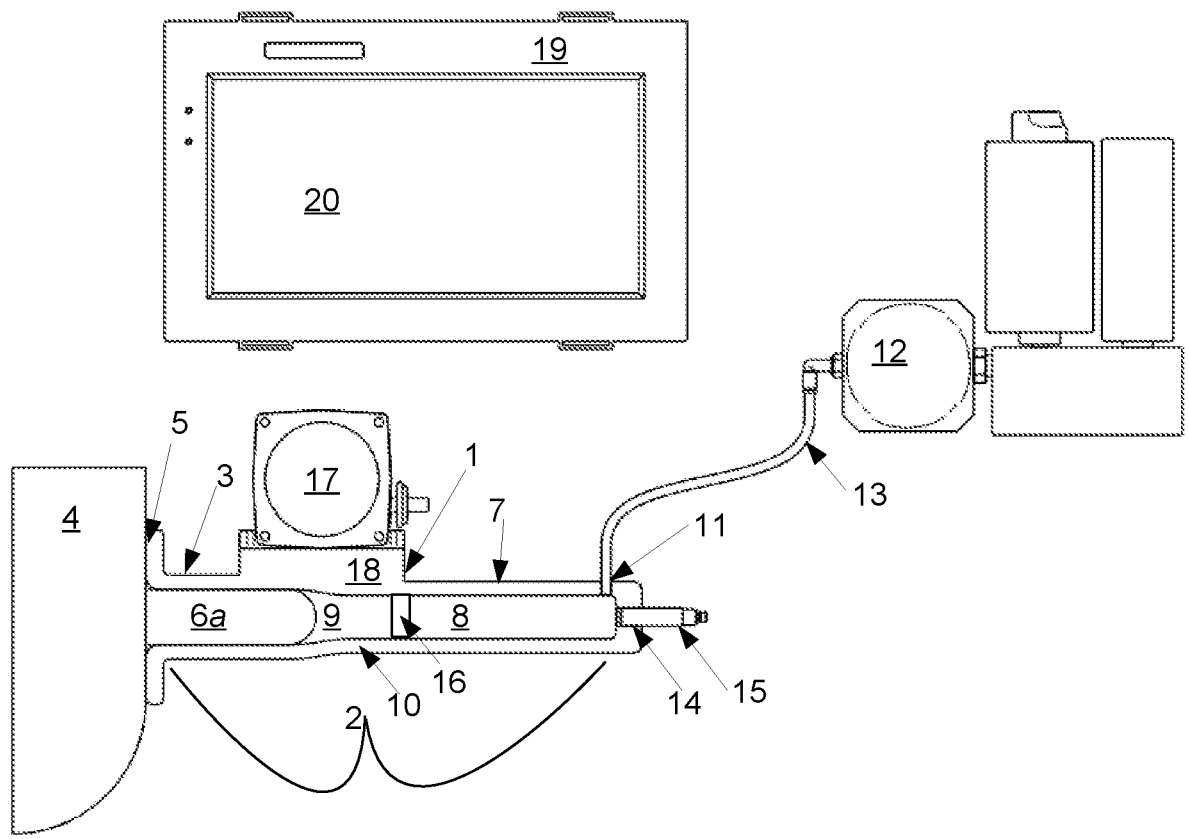
FIG. 1 shows an overview of the apparatus.

FIG. 1 shows an overview of the apparatus. Components center around the activation module 1 so as to allow delivery of vacuum and vibration in ordered combination. The vacuum chamber 2 forms a generally cylindrical or near cylindrical space inside the activation module with circumference sufficient to comfortably admit a human penis. The proximal end 3 of the activation module is adjacent the torso 4 of the user of the apparatus and has a fluted opening 5 that can rest flush against the user's torso. A stylized depiction of a human penis 6a is shown occupying the proximal portion of the vacuum chamber.

The distal end 7 of the activation module is, in use, further from the user's torso. The distal portion 8 of the chamber has a narrower interior circumference than does the proximal portion 9 of the chamber. There is therefore necessarily a chamber transitional portion 10 from the proximal portion to the distal portion of the vacuum chamber wherein the interior circumference tapers, undergoing narrowing.

The distal portion of the chamber is used to form vacuum and therefore features a vacuum aperture 11 through which a vacuum pump 12 operates. In the illustration, the vacuum pump is connected through the vacuum aperture via a vacuum hose 13. Also indicated in the distal end of the activation module is a sensor aperture 14 which fits an internal range finder, proximity sensor, radiative sensor or similar type of distance measuring sensor 15. A sensor ranging target puck 16 is disposed in the distal portion of the vacuum chamber, providing a flat surface for the internal range finder.

Also centered around the activation module is a vibration motor 17 capable of being controlled to variable frequency and amplitude. In the illustration, the vibration motor is shown mounted directly to the exterior of the activation module via a mounting bracket 18 integral to the activation module.

The vacuum pump and vibration motor are operated together as an integrated system via a control module 19, depicted here as an electronic device with touch screen control 20.

Figure 2:
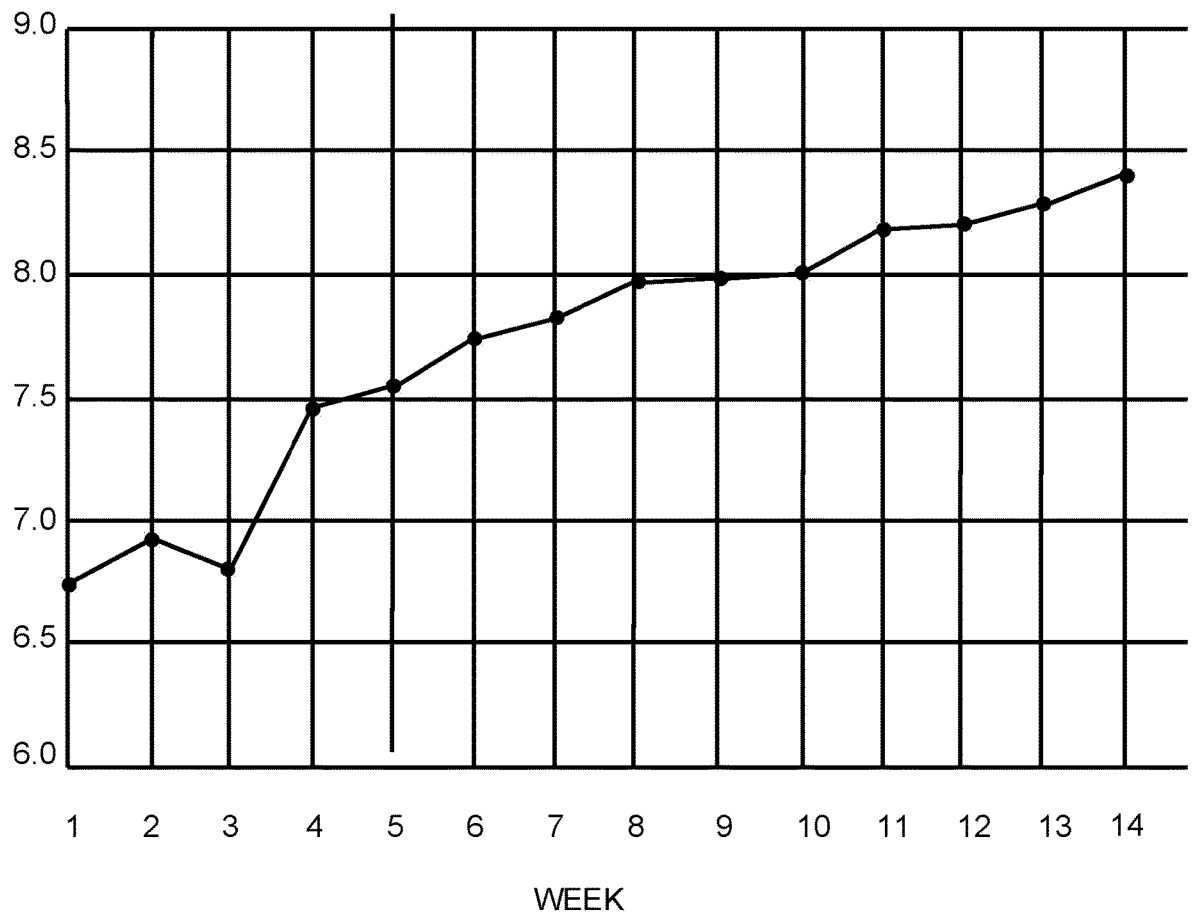
FIG. 2 depicts a chart of example results from a single course of fourteen weeks using the apparatus of the invention.

FIG. 2 depicts a chart of example results from a single course of fourteen weeks using the apparatus of the invention. The chart shows measured length under the confluence of appropriate vacuum and vibration according to the methods of the invention. Measured penis length increases when vibration interval with appropriate vibration parameters is applied after the pre-vibration, or tensioning, length is reached. Additional lengthening begins immediately upon resumption of the next cycle, using incremented cycle vacuum parameter. Example results shown are averages of the measurements taken from the last cycle in every multiple cycle use session during a week.

The chart shows an average of 1.7 inch increase in measurement after fourteen weeks of use. The increased average length measured is under the appropriate vacuum tensioning plus vibration according to the invention. When tensioning plus vibration is removed, approximately 25% of the increased length is retained long term. In this example, 0.425 inches in lengthening is retained as new penile tissue growth.

Figure 3:
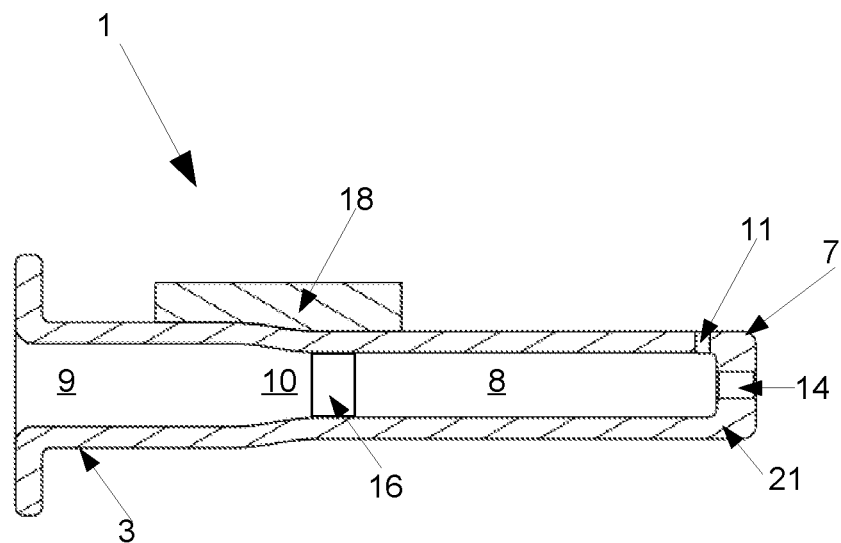
FIG. 3 is a detail view focusing on the activation module of the apparatus.

FIG. 3 is a detail view focusing on the activation module 1 of the apparatus. The case wall 21 of the activation module is strong enough to contain at least 56% interior vacuum at standard external atmospheric pressure. The case wall at the proximal end expands into a fluted or flanged opening. The vacuum chamber proximal portion 9, shown here empty, is able to be seen narrowing into the vacuum chamber distal portion 8 via the vacuum chamber transitional portion 10. The sensor target puck 16 disposed in the vacuum chamber of the activation module is only a few thousandths of an inch smaller in circumference than the distal portion 8 circumference, such that it will not rattle or become displaced.

The distal portion 8 of the vacuum chamber must necessarily extend beyond any expected distance to which a human penis can be extended by use of the apparatus, with enough room beyond that to form vacuum. Thus, an embodiment of the apparatus might have a proximal vacuum chamber portion 9 of fourteen inches or more in length. The distal vacuum portion 8 of the chamber extends beyond that for enough chamber volume to allow at least 56% vacuum to be generated in the vacuum chamber using the connected vacuum pump.

In this instant illustration, the vacuum aperture 11 leading into the distal portion 8 of the chamber is depicted as through the upper, dorsal side of the activation module case wall 21. The sensor aperture 14 is depicted as through the closed distal end 7 of the activation module case wall. In alternate embodiments, these apertures can be located so as to lead into the distal portion of the chamber through other locations in the activation module case wall.

The vibration motor mounting bracket 18 is illustrated as sitting dorsally, on top, of the activation module exterior, but can be located ventrally, below, or elsewhere. The chamber transitional portion 10 in the pictured embodiment shows the internal chamber circumference narrowing accompanied by a related narrowing of the external chamber case wall; however, in other embodiments the external case does not reflect the shape of the internal vacuum chamber.

In one embodiment of the invention, the activation module 1 is made of clear polycarbonate tubing, with ruler markings, allowing the user to observe progress. In this embodiment, the proximal 3 and distal 7 ends of the activation module are manufactured in separate pieces and mated together. The closure of the distal end in this embodiment is manufactured as a threaded end cap, with machined locking slots and locking buttons mating the end cap to the distal end. A gasket between the mating faces of the end cap and the distal end is used to prevent vacuum leakage.

Figure 4:
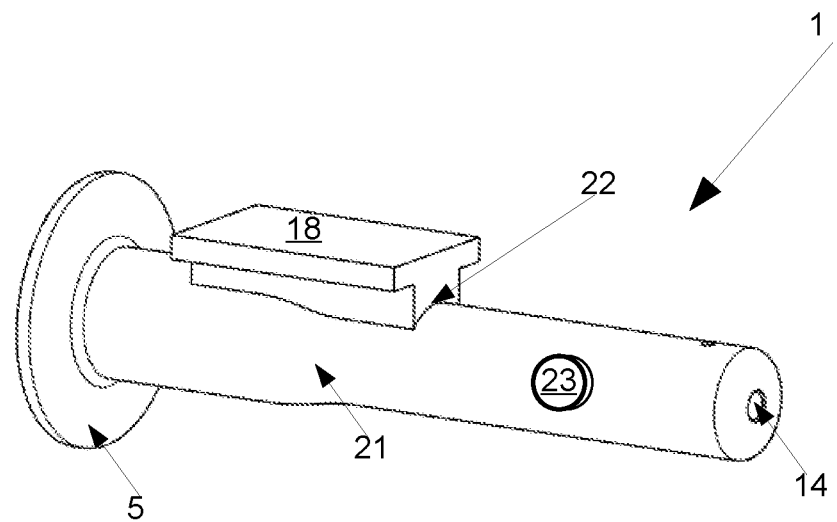
FIG. 4 is a perspective view of the exterior of the activation module portion of the invention.

FIG. 4 is a perspective view of the exterior of the activation module of the invention. In the depicted embodiment, the exterior of the of activation module 1 is essentially cylindrical and the flanged opening 5 is circular.

The mounting bracket 18 for the vibration motor is depicted as having an I-beam type shape in order to accommodate mounting bolts. The bottom of the mounting bracket 22 is curved flush with the cylindrical exterior of the activation module so as to transmit vibration to the chamber.

A manual vacuum release valve 23 is disposed on the exterior of the activation module, through the case wall 21. This release valve does not stop the vacuum pump from operating, but it allows escape of air into the activation module faster than the vacuum pump produces vacuum, thus acting as a manual emergency pressure release. Two additional user-activated vacuum release controls are disposed on the control module, as explained below in regard to FIG. 11.

Figure 5:
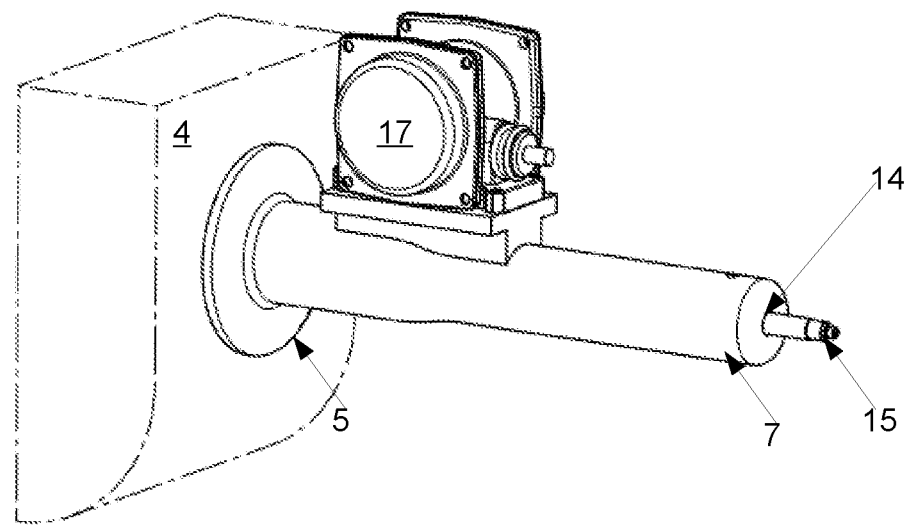
FIG. 5 is a perspective view of the exterior of the activation module illustrating three aspects of the invention.

FIG. 5 is a perspective view of the exterior of the activation module illustrating three aspects of the invention. The controllable vibration motor 17 is shown mounted on the mounting bracket so as to transmit vibration through the activation module case wall. A pulse-width-modulation controllable vibration motor can be used, or a pneumatic vibration motor, or other suitable vibration motor capable of supplying amplitudes in the specified ranges. Second, the internal range finding sensor 15 is depicted as in use, occupying the sensor aperture 14 in the distal end 7 of the activation module. Third, the flanged opening portion 5 is flush against the user's torso 4 so as to allow a vacuum seal.

Figure 6:
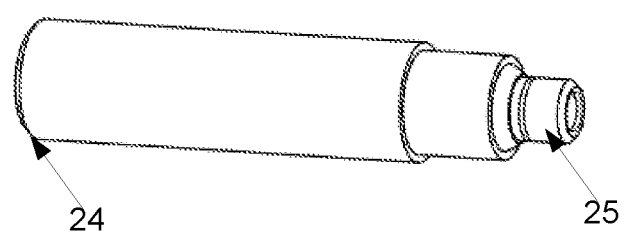
FIG. 6 is a perspective view of an internal range finder component as used in the invention.

FIG. 6 is a perspective view of an internal range finder component as used in the invention. The internal range finder, also called a proximity sensor, is a sensor used to determine the distance between the distal end of the activation module and the end of the user's penis. In the preferred embodiment, this sensor is an ultrasonic proximity sensor that does not produce enough energy to affect the user's tissue. In other embodiments, an infrared sensor, laser or other radiative sensor can be used. The proximal end 24 of this component is sized to fit into the sensor aperture. The distal end 25 of the component accommodates a wire for connection to the control module.

Figure 7:
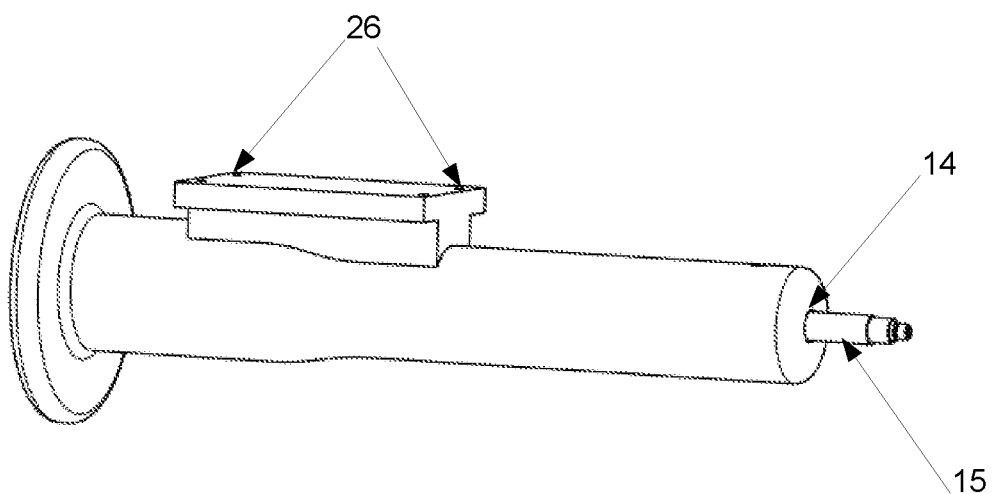
FIG. 7 is an additional perspective view of the exterior of the activation module portion of the invention.

FIG. 7 is an additional perspective view of the exterior of the activation module portion of the invention. The proximity sensor 15 is located in the sensor aperture 14 as seen from the outside. Additionally, the mounting bracket is shown with mounting bolt holes 26 extending through horizontally extended portions of the mounting bracket. In the preferred embodiment, the activation module is constructed of a hardened plastic using an injection molded or 3D-printed technique to achieve the required shape.

Figure 8:
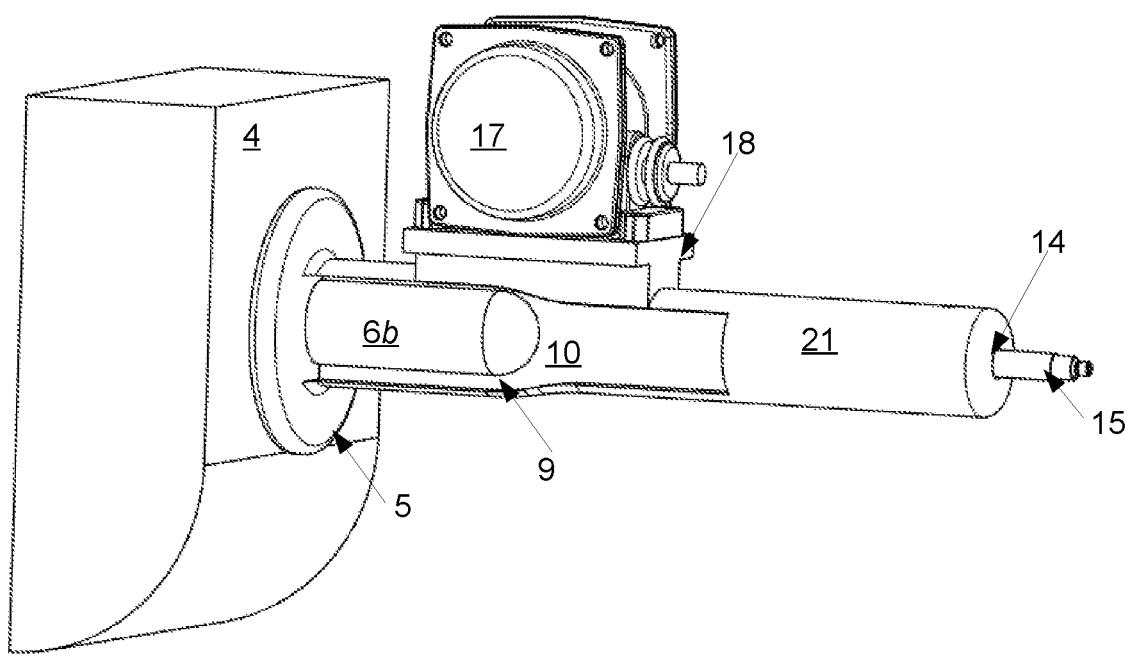
FIG. 8 is a perspective view of the exterior of the activation module with a cut-away view of the activation module.

FIG. 8 is a perspective view of the exterior of the activation module with a cut-away view of the activation module. The vibration engine 17 is disposed on the mounting bracket 18. The range sensor 15 is disposed in the sensor aperture. The flanged opening portion 5 is flush against the user's torso.

The cutaway view through the case wall 21 of the activation module portrays a stylized human penis at rest 6b, reaching into the proximal portion 9 of the vacuum chamber. Said penis is not subject to vacuum in the chamber and thus not inflated. Not thus inflated, it does not contact the ventral interior of the case wall. This allows an unobstructed view of transitional portion of the activation module interior.

Figure 9:
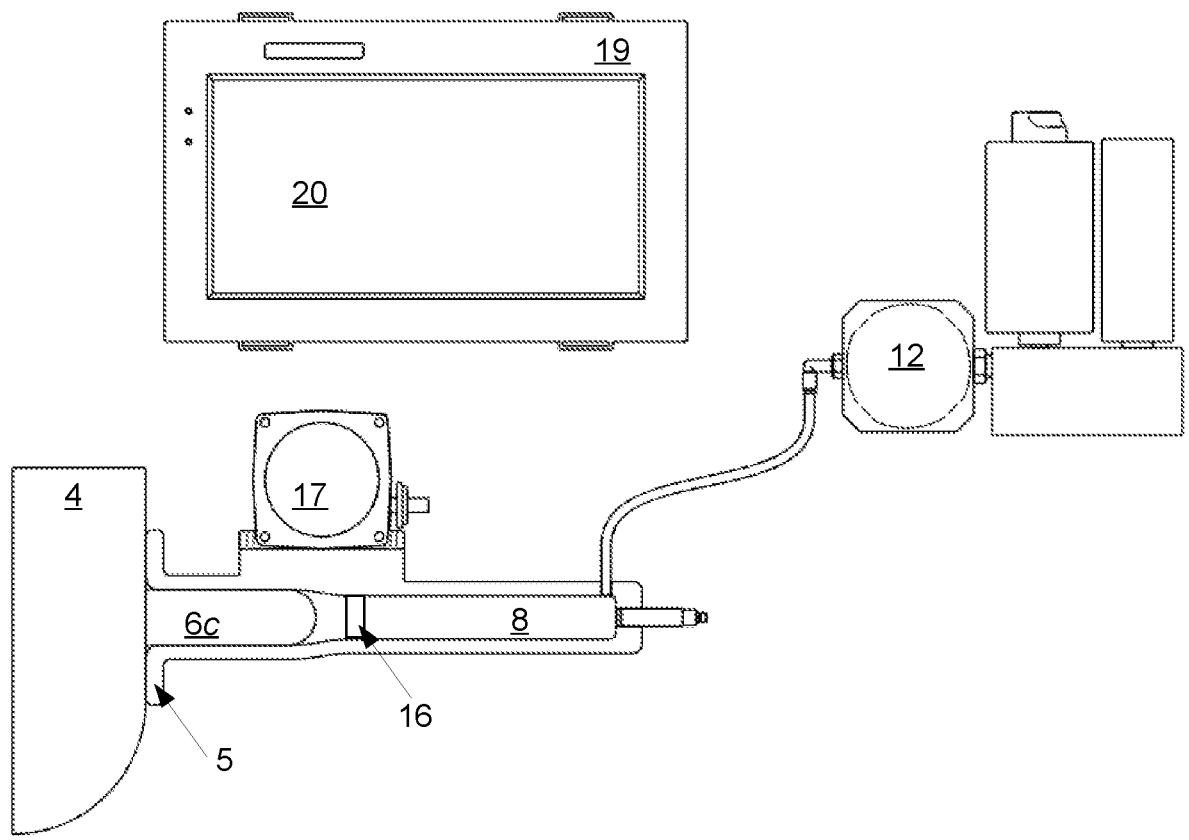
FIG. 9 is a side view of the preferred embodiment of the apparatus in the initial stage of use.

FIG. 9 is a side view of the preferred embodiment of the apparatus in the first stage of use. To begin, a set of control parameters are stored in the control module 19 having a persistent, non-volatile memory. In the preferred embodiment, shown here, the control module features a touch screen 20 for user input and is referred to as a control panel. In other embodiments, the control module can use buttons, dials or other common inputs. In another embodiment, the control module can also be capable of receiving user input via a paired smartphone, computer or other smart device.

Control parameters stored in the control module are used to determine how the control module controls the vibration motor 17 and vacuum pump 12. Control parameters stored in the control module can include the following: vacuum parameters which set levels of vacuum produced by the vacuum pump; vibration frequency parameters which set frequencies of vibration produced by the vibration motor; vibration amplitude parameters which set magnitudes of vibration produced by the vibration motor; time parameters which can determine durations of vacuum produced by the vacuum pump; time parameters which can determine durations of vibration produced by the vibration motor; increment and decrement parameters which set how much to increase or decrease other parameters cyclically; and maximum or minimum parameters which set maximum or minimum limits on other control parameters.

For this step of setting a value for at least one control parameter of the apparatus, the set of control parameters for which a value can be set may include:
  a first tensioning interval vacuum parameter;
  a first tensioning interval duration parameter;
  a first vibration interval frequency parameter;
  a first vibration interval amplitude parameter;
  a first vibration interval duration parameter;
  a first recovery interval vacuum parameter;
  a first recovery interval duration parameter,
  a second tensioning interval vacuum parameter;
  a second tensioning interval duration parameter;
  a second vibration interval frequency parameter;
  a second vibration interval amplitude parameter;
  a second vibration interval duration parameter;
  a second recovery interval vacuum parameter;
  a second recovery interval duration parameter;
  a vacuum increase parameter;
  a duration increase parameter;
  a duration decrease parameter;
  a vibration frequency increase parameter;
  a vibration frequency decrease parameter;
  a vibration amplitude increase parameter;
  a vibration amplitude decrease parameter;
  a seal parameter;
  a maximum vacuum parameter;
  a user target vacuum parameter.

In the preferred embodiment of the invention, the maximum vacuum level parameter is set at, or around, 56.8% vacuum. This is the maximum vacuum level allowable in the activation module for safety.

Also in the preferred embodiment of the invention, multiple control parameters can be set by the user. User determined control parameters are received from the user into the control module via touchscreen, buttons, dials, paired device or other appropriate input means. In the preferred embodiment, the user may input a user-target vacuum parameter which is lower than the maximum vacuum level parameter. Note that, regardless of settings for the maximum vacuum parameter and the user target vacuum parameter, there will necessarily be a cycle wherein a first tensioning interval vacuum parameter is lower than the highest vacuum parameter that is reached on the following cycle—whether that highest vacuum parameter is the maximum vacuum parameter or a user target vacuum parameter.

In the method of using the apparatus, the user's penis is received into the proximal opening of the vacuum chamber of the apparatus. Here, the user's relaxed penis 6c is depicted. Because the user's penis is at rest, it is shown as not yet in contact with the sensor ranging target puck 16 disposed in the distal portion 8 of the vacuum chamber. In the preferred embodiment, the user starts the activation module using the control panel. In an alternate embodiment, the control module starts the activation module upon detecting, using the internal range finder, that the user's penis is in the proximal portion of the vacuum chamber.

Starting the activation module means that the vacuum pump 12 is set to produce vacuum in the activation module sufficient to form a vacuum seal around the base of the user's penis in the activation module and/or between the proximal opening 5 and the user's torso 4. In the preferred embodiment, the vacuum pump produces vacuum effect via air pumping methods rather than water or liquid pumping. The amount of vacuum required to form the vacuum seal is stored in the control module as a seal parameter. A sufficient value for the seal parameter has been found to be around 20% vacuum.

Figure 10:
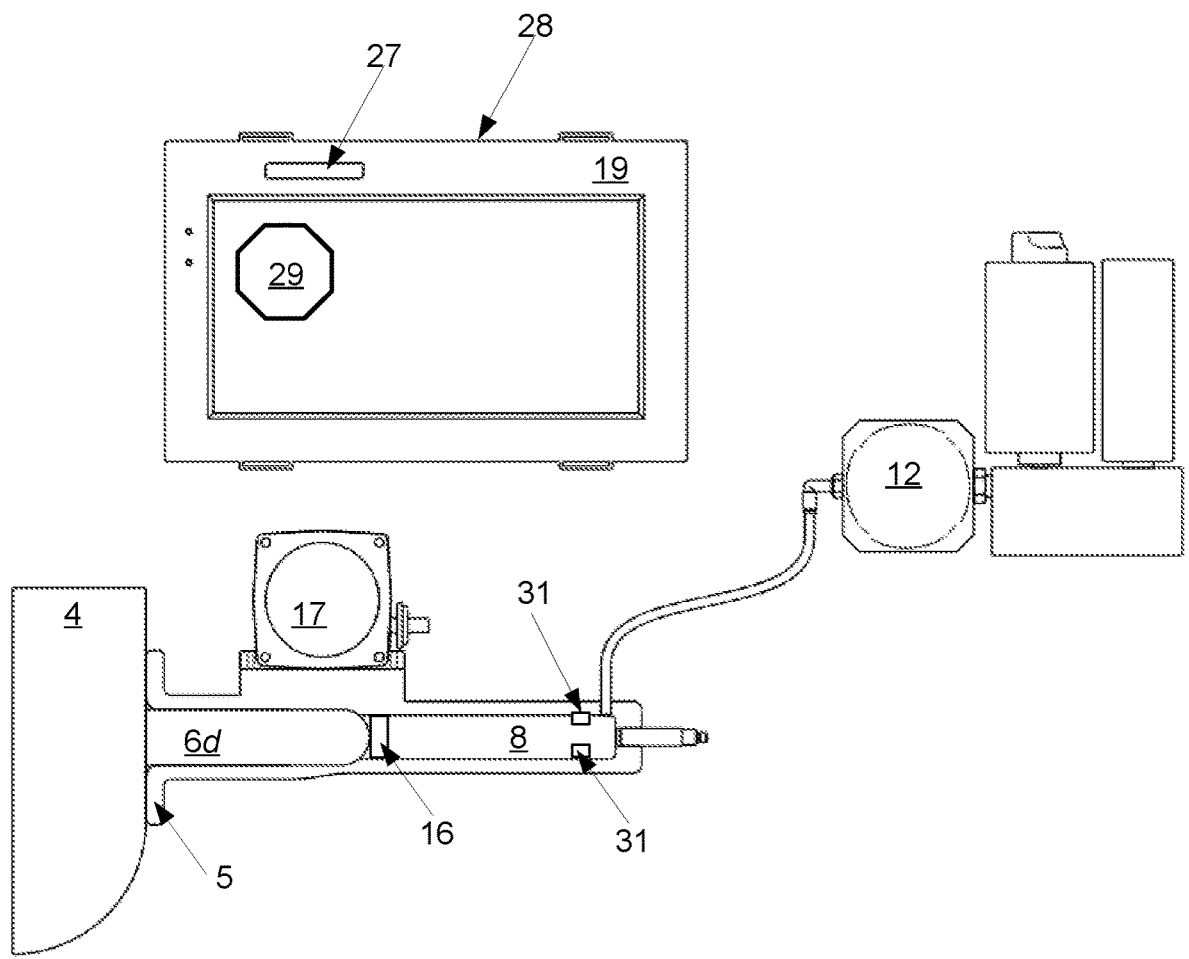
FIG. 10 is a side view of the preferred embodiment of the apparatus in the tensioning interval step of a cycle of using the invention.

FIG. 10 is a side view of the preferred embodiment of the apparatus in the tensioning interval step of a cycle of using the invention. In this stage of use, a tensioning interval is caused in the vacuum chamber, a tensioning interval having a first tensioning interval vacuum parameter and a first tensioning interval duration parameter.

For a first tensioning interval, the control module 19 controls the vacuum pump 12 to produce in the activation module a level of vacuum according to a first tensioning interval vacuum parameter. The vacuum produced is meant to be sufficient to cause the user's penis to be tensioned, such that it is made to swell or to become turgid or to fill with blood. Tensioned, the user's penis is encouraged to increased length and increased circumference.

The Figure illustrates the user's penis fully tensioned to a first length due to vacuum 6d. As can be seen, the penis is elongated in comparison to its depiction in FIG. 9. Additionally, the penis is of greater circumference in comparison to the depiction of FIG. 9. The narrowing transitional portion of the vacuum chamber leading into the narrow distal portion of the vacuum chamber helps prevent the skin of the user's penis from being pulled forward, due to vacuum, under the glans. Because the user's penis is tensioned, it comes into contact with the sensor ranging target puck 16 disposed in the distal portion 8 of the vacuum chamber.

In the preferred embodiment, the user's penis is held in this tensioning interval for ten seconds. The vibration interval begins at or just after the tensioning interval begins, and the cycle proceeds as vacuum in conjunction with vibration as described below in regard to FIG. 11.

This first tensioning interval has a duration equal to a first tensioning interval duration parameter stored in the control module. In an alternate embodiment, this first tensioning interval has a duration parameter received from the user.

In an alternate embodiment, the user's penis is held in this tensioning interval long enough that the internal range finding sensor 15 can determine it has stopped increasing in length due to vacuum, thus determining the penis is fully tensioned due to vacuum for this cycle. The vibration interval is commenced subsequent to said first determination by said sensor that the penis is fully tensioned. The length measured via said sensing is stored in the control module as tensioning length data for this cycle. The time required to reach this length is recorded in the control module as tensioning time data for this cycle. A subsequent tensioning interval may have a duration equal to this tensioning time data stored in the control module and increased by a tensioning stepwise duration increase parameter.

It is understood that the tensioning interval of this step of the method of the invention leads to the cells of the user's penile tissue entering what is referred to here as a tensioned state. As has been described above, the penile tissue cells in the tensioned state as during this tensioning interval can be envisioned as taking on a tensioned or elongated or elliptical shape in the direction of the vacuum, with all of the cell-to-cell bonds remaining intact. This elliptical distortion can remain as long as the tension remains. Thus, the step of causing a first tensioning interval in the vacuum chamber uses a vacuum parameter sufficient to cause at least some cells of the user's penis to be stretched to an elliptical shape via vacuum tension.

Two user-activated vacuum release controls are disposed on the control module. One such user-activated vacuum release control is a manually actuated electric button or switch 27 disposed on the casing 28 of the control module that is operatively configured so as to shut off the vacuum pump 12. Another such user-activated vacuum release control is a screen button 29 in the interface screen of the control module that is configured to shut off the vacuum pump.

The control module is wired to a hold solenoid and a release solenoid which close and open, respectively, the vacuum pump. As a safety measure, the solenoids are configured so as to be normally open. If the apparatus loses power, any existing vacuum is released. The electrical release controls are also wired to the solenoids so as to immediately release any existing vacuum when triggered.

As a further vacuum safety measure, a first vacuum sensor 30 and an auxiliary vacuum sensor 31 are disposed in the vacuum chamber, or else operatively connected to the vacuum chamber or vacuum line. These two vacuum sensors are operatively connected to the control module and provide vacuum readings to the control module. If vacuum sensor readings indicate the target vacuum for the current cycle is reached, the vacuum pump is stopped and held at vacuum. If vacuum sensor readings indicate that maximum vacuum has been exceeded, the vacuum pump is stopped and released, allowing air into the vacuum chamber. Further, if the first vacuum sensor and auxiliary vacuum sensor readings differ by more than 3%, the vacuum pump is stopped and released, allowing air into the vacuum chamber, and the vibration motor is stopped.

Figure 11:
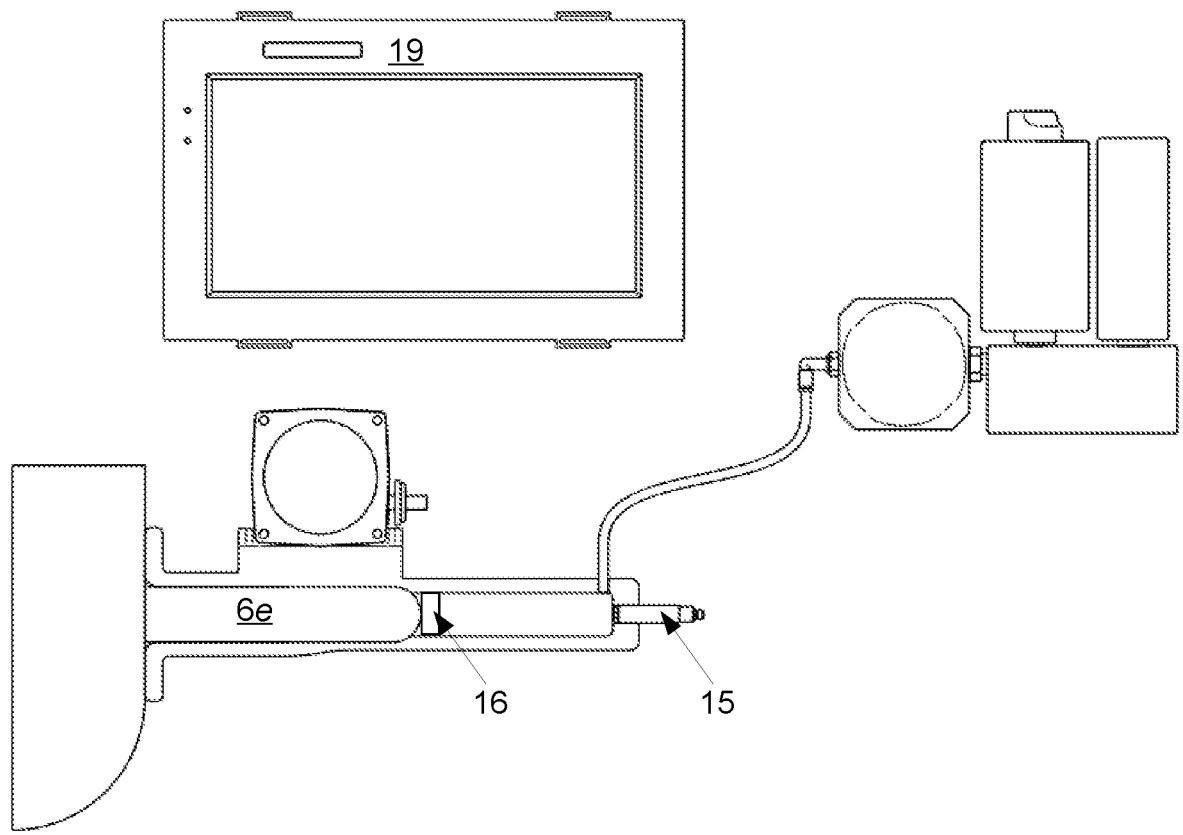
FIG. 11 is a side view of the preferred embodiment of the apparatus in a first vibration interval step of the invention.

FIG. 11 is a side view of the preferred embodiment of the apparatus in a first vibration interval stage of use. In the preferred embodiment, the step of causing a vibration interval begins approximately at the same time as, or just after, the beginning of the tensioning interval. In an alternate embodiment, the vibration interval begins after the user's penis reaches tensioning length, as described above in regard to FIG. 10, in which case the step of causing a first vibration interval begins after at least some cells of the user's penis are fully stretched due to the first tensioning interval. It is possible to begin vibration prior to beginning vacuum tensioning, but the goal is a concurrence of the tensioning interval and the vibration interval such that at least a portion of the duration of the vacuum tensioning interval overlaps with at least a portion of the duration of the vibration interval.

For this first vibration interval, the control module controls the vibration motor to produce vibration in the activation module, in conjunction with vacuum from the tensioning interval overlapping in duration. In the preferred embodiment, vibration is produced according to a first vibration interval vibration frequency parameter and a first vibration interval vibration amplitude parameter. Vibration amplitude may be set in terms of distance per second of the activation module, in terms of 'G' as acceleration from gravity, force due to acceleration or other term used in the art to measure vibration power.

A National Institute of Health study found that whole-body vibration can be tolerated for up to one minute at approximately 2.0 g by standing adults ("Safety and severity of accelerations delivered from whole body vibration exercise devices to standing adults"[1] located at https://www.ncbi.nlm.nih.gov/pmc/articles/PMC3688642). Amplitude in the vibration motor moving an eccentric mass 0.94 inches per revolution at 3600 RPM gives a vibration amplitude in approximately 123G for the motor eccentric mass, with G (or g's) being amplitude measured in terms of acceleration due to gravity, or 9.8 m/s$^2$. When the vibration motor is applied to a 4 killogram mass consisting of the motor, the activation module and the user's penis, a vibration amplitude of approximately 9.2G RMS (root mean square) can be expected. Testing indicates this approximates the high end of tolerable vibration amplitude to the user's penis and is effective for tissue increase in seven to ten second vibration intervals. Similarly, the lowest vibration amplitude in a mass consisting of the motor, the activation module and the user's penis expected to have useful effect in the invention is approximately 2.1G RMS.

In the preferred embodiment, the effective vibration should have a minimum of approximately 0.69 mm peak to peak at 3600 RPM, or 3.5 g's RMS. Also in the preferred embodiment, the effective vibration should have a maximum of approximately 1.7 mm peak to peak at 3600 RPM, or 8.7 g's RMS for short intervals of approximately ten seconds. A best mode effective amplitude in the preferred embodiment is 1.2 mm peak to peak at 3600 RPM, or 6.1 g's RMS for vibration intervals. Different vibration amplitude and frequency settings can be used to achieve similar effects.

Thus, concurrent with the first tensioning interval, a first vibration interval is applied in the vacuum chamber, the first vibration interval having a first vibration interval duration parameter, the first vibration interval being applied via a vibration motor having a first vibration interval frequency and a first vibration interval amplitude.

The vibration produced, in conjunction with the vacuum, is meant to be sufficient to cause the user's penis to swell further in the activation module. Under the described application of vacuum in conjunction with vibration, the user's penis is encouraged to increased length beyond that induced solely from vacuum. Similarly, the invention's application of vibration in conjunction with vacuum encourages the user's penis to expand in circumference over and beyond the expansion from vacuum alone described according to FIG. 10. Because the user's penis is encouraged to further length, it comes into contact with the sensor ranging target puck disposed in the distal portion of the vacuum chamber, pushing it forward. The proximity sensor target puck provides a flat surface that the internal range finder can use as a target to measure elongation of the penis at appropriate steps of the invention.

FIG. 11 illustrates the user's penis so expanded under vacuum and vibration 6e. In the preferred embodiment, the vibration interval lasts approximately seven seconds, ending three seconds prior to the end of the concurrent tensioning interval. These three seconds without vibration allow the measuring target puck 16 to stop moving, so that the internal range finder 15 can accurately determine the length that the user's penis reached under the vibration interval. This length is stored in the control module as vibration length data for this cycle.

In an alternate embodiment, the user's penis is held in this vibration interval for long enough that the internal range finder makes a determination that the penis is fully tensioned to a length due to vacuum in combination with vibration, such that the penis has stopped increasing in length due to vibration plus vacuum, with the recovery interval commenced after. This vacuum tensioning length is stored in a persistent, non-volatile memory of the control module as vibration length data for this cycle. The time required to reach this length is recorded in the control module as vibration time data for this cycle. A subsequent vibration interval may have a duration equal to this vibration time data stored in the control module and increased by a vibration stepwise duration increase parameter.

In an alternate embodiment, variations in vibration parameters, such as vibration frequency or vibration amplitude, may be set by the control module or from user input. When variations in vibration parameters are used, they may be stored as vibration interval frequency data and amplitude data. In conjunction with vacuum data, tensioning length data, vibration length data, interval durations and with analysis of many cycles of such data, the most effective combinations of vacuum, vibration amplitude, vibration frequency, interval durations and number of cycles can be determined.

Applying vibration before the tissue is tensioned by vacuum is ineffective. This vibration interval step of the method of the invention, performed concurrently with the tensioning interval step of the method of the invention, is what works to induce the expected micro-tearing between cells of the penile tissue, creating room for new cell growth in the areas of cell tearing. Thus, the step of causing a first tensioning interval, in conjunction with the step of causing a first vibration interval, is sufficient to cause micro-tears in at least some tissue of the user's penis.

In consequence of this tensioning, tearing and formation of new cells, the user may expect growth, additional mass and/or re-growth of penile tissue. Thus, the step of causing a first tensioning interval, in conjunction with the step of causing a first vibration interval, is sufficient to encourage formation or addition of at least some new cells in the tissue of the user's penis.

Figure 12:
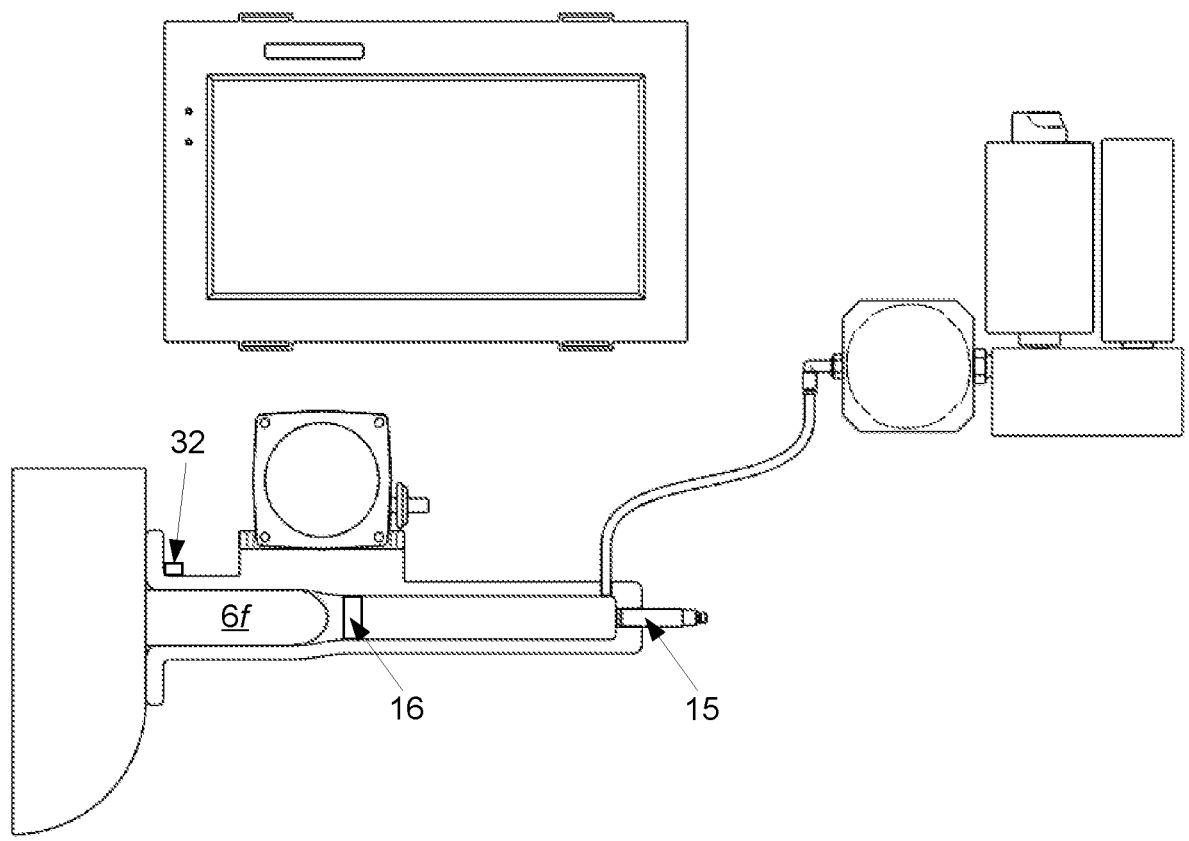
FIG. 12 is a side view of the preferred embodiment of the apparatus in the recovery interval step of a use cycle of the invention.

FIG. 12 is a side view of the preferred embodiment of the apparatus in the recovery interval stage of a use cycle. Vibration from the vibration interval is ceased or reduced and the vacuum level in the vacuum chamber is reduced to a level below the prior tensioning interval level after elapse of the tensioning interval duration parameter, causing a first recovery interval in the vacuum chamber. The recovery interval has a recovery interval vacuum parameter and a recovery interval duration parameter, with the recovery interval vacuum parameter being lower than the prior tensioning interval vacuum parameter. In the preferred embodiment, this recovery interval vacuum is around 20% or enough maintain a vacuum seal. In alternate embodiments, a recovery interval vacuum parameter can be as low as 10% or as high as 30%.

The vacuum parameter of the recovery interval is not high enough to induce micro-tearing in the tissue of the user's penis. In the preferred embodiment, the recovery interval is held for five seconds. The user's penis 6f is shown retracted as compared with the vibration interval of FIG. 11, above, but also expanded in comparison with the prior interval of FIG. 9, above. At low vacuum, this duration is such that the user's penis can quickly reach tensioning length for the tensioning interval of the next cycle. A duration that does not depart effectively from this effect can be used in alternate embodiments. The step of causing a first tensioning interval, in conjunction with the step of causing a first vibration interval, followed by the step of a recovery interval, is sufficient to encourage formation or addition of at least some new cells in the tissue of the user's penis.

After the recovery interval, a new cycle of tensioning interval, vibration interval and recovery interval is initiated by starting a new tensioning interval. The vacuum for the new cycle is increased by the stepwise vacuum increase parameter as explained above. In the preferred embodiment, the number of cycles parameter is forty. Also in the preferred embodiment, the stepwise vacuum increase parameter is 4%, such that the tensioning interval vacuum goes from 20% to 56% in nine cycles. These parameters can vary or be altered by the user in alternate embodiments.

In an embodiment of the invention which includes pelvic floor muscle tensioning exercise, said exercise can be performed during a tensioning interval with high vacuum, during a recovery interval with lower vacuum, or during an interval specific to pelvic floor exercise with enough vacuum to keep the vacuum chamber of the activation module sealed to the body of the user.

Where the user is tensioning his pelvic floor muscles against the pull of the vacuum, without vibration, the movement of the sensor target puck 16 can be picked up by the internal range finding sensor 15 as measuring a pelvic tensioning. In this embodiment, the internal range finding sensor can be referred also as a pelvic tensioning sensor disposed on or in the activation module portion, operatively coupled to the control module portion, capable of detecting pelvic muscle exercise by a user of the apparatus. Alternately, the weight of the activation module, sealed to the user's body by vacuum, can act as resistance for pelvic tensioning exercise by the user. In this use case, movement of the activation module can be measured using an accelerometer 32 acting as a pelvic tensioning sensor in or operatively connected to the activation module and to the control module. In either case, such sensor measurements can be stored in the memory of the control module as pelvic floor muscle exercise data. Such pelvic floor muscle exercise data can include the number of pelvic floor muscle contractions, velocity or acceleration of said contractions and distance contracted. This pelvic floor muscle exercise data can be compared over one use cycle to another, giving the user of the invention an indication of pelvic floor muscle strengthening due to exercise using the apparatus of the invention.

Figure 13:
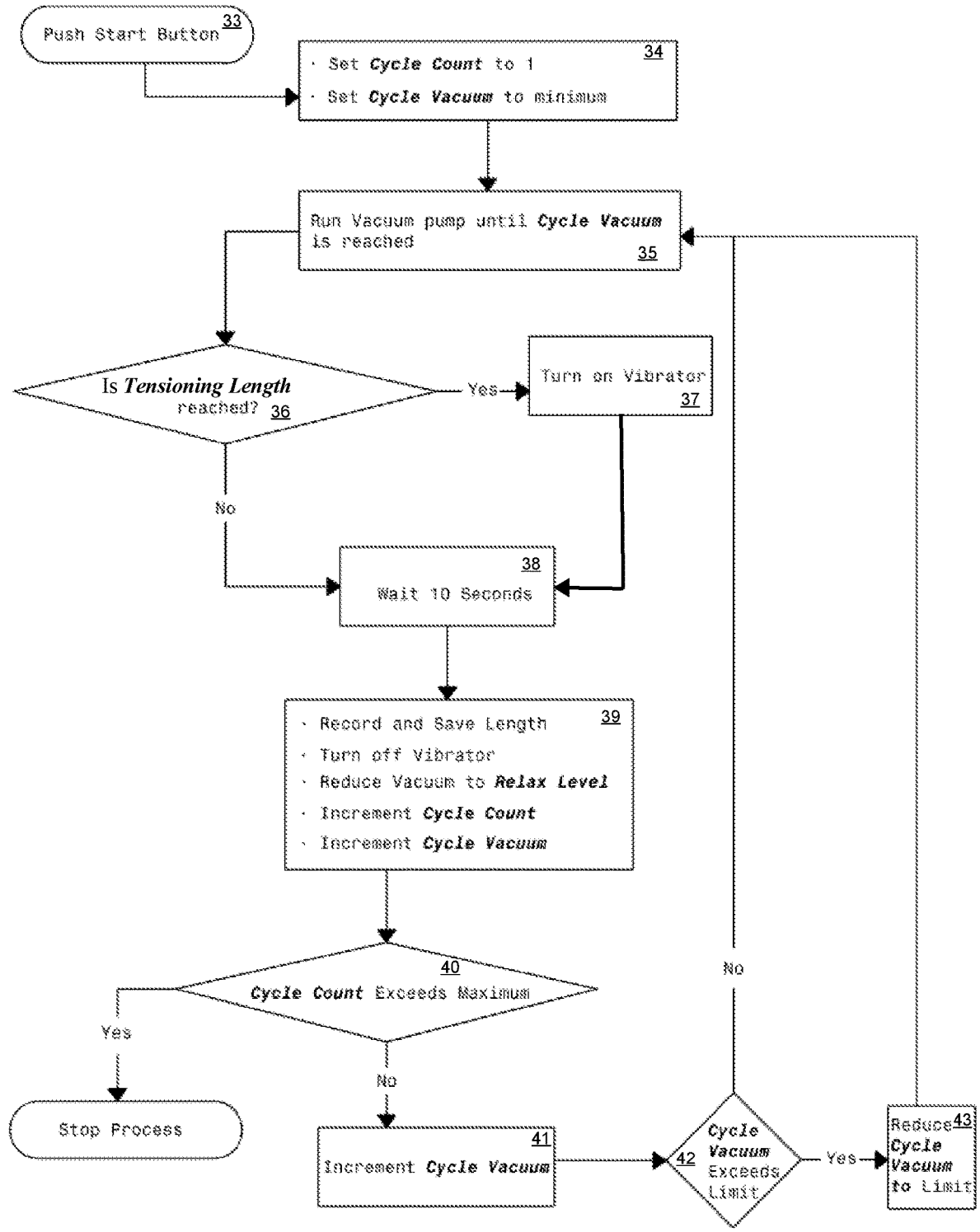
FIG. 13 depicts a flowchart explaining an operation of the apparatus in an illustrative embodiment of the invention.

FIG. 13 depicts a flowchart explaining an operation of the apparatus in an illustrative embodiment of the invention. The user, with his penis in the activation module, presses a Start control connected with the control module and the activation module is depressurized according to the vacuum seal parameter in step 33.

In step 34, the control module sets a Cycle Count to 1, initiating a first cycle in a use of the apparatus. A Cycle Vacuum level is set to a predetermined minimum value in the control module. Cycle Vacuum level can be referred to for purposes of the disclosure as a first tensioning interval vacuum parameter.

In step 35, the vacuum pump is then run until the Cycle Vacuum level is achieved in the activation module, initiating a first tensioning interval in this first use cycle. Through use of the internal range finder, it is determined in step 36 whether Tensioning Length has been achieved. Tensioning Length is the user's penis tensioned to as much length as will be induced by the current Cycle Vacuum level.

Next, in step 37, once the user's penis has reached Tensioning Length, the vibration motor is turned on to an amplitude and frequency set by the user, or else to a predetermined amplitude and frequency. The vacuum pump continues for ten seconds in step 38. In the embodiment depicted by this flowchart, it can be seen that the vibration motor will turn on during the ten seconds of step 38, since the user's penis reaches tensioning length quickly after vacuum commences. In other embodiments, vibration simply initiates with or just after vacuum, irrespective of vacuum-induced tensioning length.

During this time, the combination of vacuum and vibration induces a further increase in length and/or circumference of the user's penis beyond the Tensioning Length. In step 39, the Vibration Length of the penis at this vibration interval is determined using the internal range finder. The Tensioning Length and Vibration Length are recorded as data in the control module, along with the Cycle Vacuum, vibration parameters, and other parameters in use for this cycle of the invention.

Also at this step, the Vibration Motor is turned off and the vacuum level is reduced to a Relax Level to initiate a recovery interval for a given duration. The recovery interval being the last phase of the cycle, a Cycle Count parameter is incremented in the control module.

The control module step 40 next determines if a maximum Cycle Count has been reached. If yes, the process is complete and no more cycles are run.

Otherwise, in the next step 41 the Cycle Vacuum is incremented, such that the tension interval vacuum for the next cycle is higher. The amount by which the Cycle Vacuum is increased can be a control module parameter that is predetermined, or one that is set by the user. The Cycle Vacuum increase amount can alternatively vary according to a formula in some embodiments. For example, the Cycle Vacuum increase will be less at higher numbers of cycles, or will be less as the recorded prior highest length of the user's penis during the tensioning interval is approached for a given cycle.

If this newly increased Cycle Vacuum does not exceed the limit for vacuum in step 42, a new cycle is begun by returning to step 35. In the preferred embodiment, there is a safety vacuum limit of approximately 56.8% vacuum, or about 334 Torr. If the newly increased Cycle Vacuum does exceed the limit, Cycle Vacuum is reduced to the limit at step 43 before a new cycle is initiated.

Figure 14:
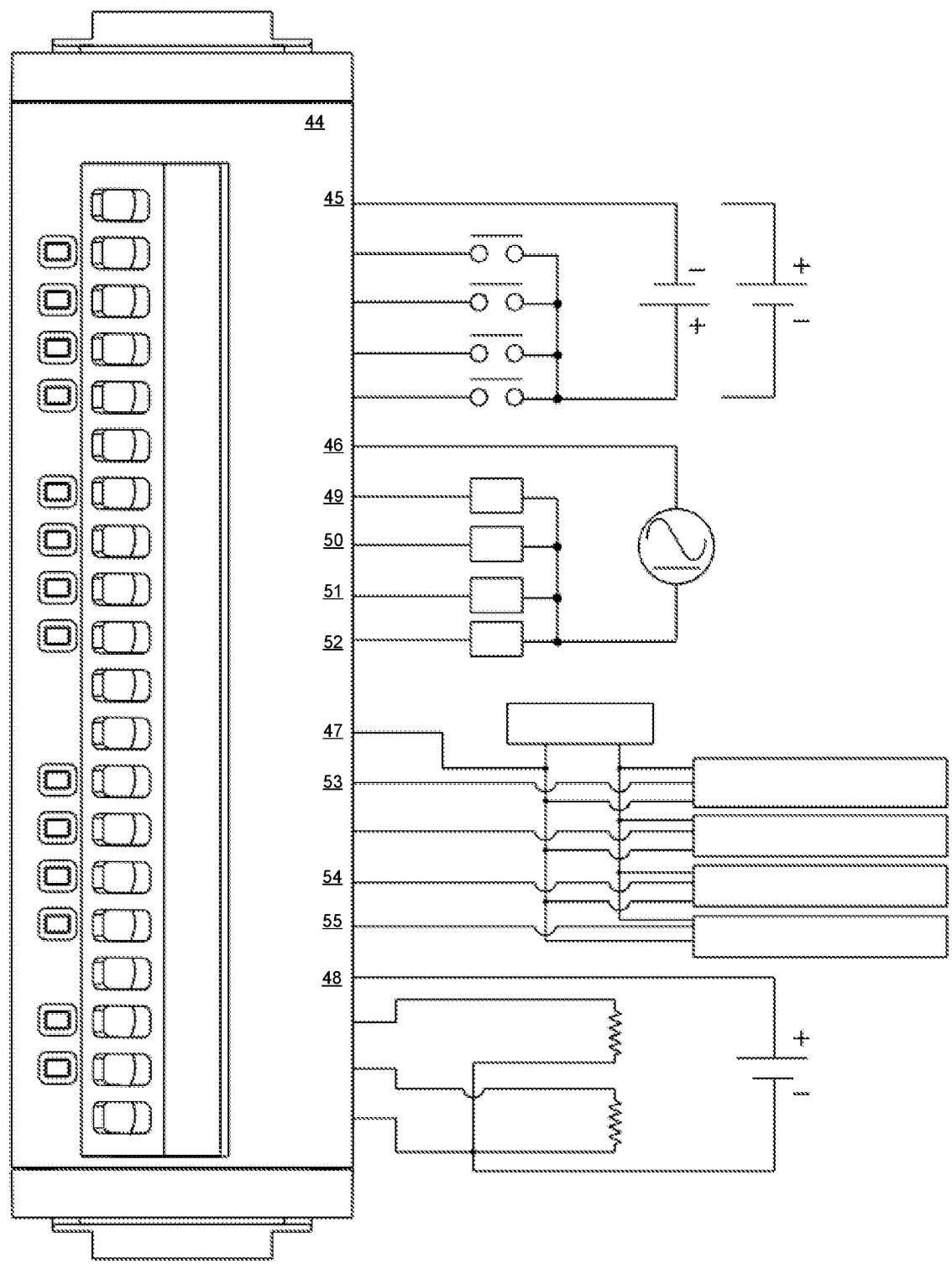
FIG. 14 depicts a wiring diagram illustrating possible electrical connections in an example embodiment of the invention.

FIG. 14 depicts a wiring diagram illustrating usable electrical connections in an example embodiment of the invention. A Click Plus brand C2-08-DR6C I/O module is depicted as a workable option for a wiring harness 44. The wiring harness features a set of channels for discrete input 45, a set of channels for discrete output 46, a set of analog input channels 47 with analog-digital conversion and a set of analog output channels 48 with digital-analog conversion.

The four discrete inputs can be wired in conjunction with a noise-cancelling capacitor to receive state signals from signal-capable components. Here, discrete signal outputs are reserved for vibration motor control signal 49, vacuum pump control signal 50, a hold solenoid signal 51 and a release solenoid signal 52. The four discrete outputs are wired in common with 120V or 240V AC.

The analog input channels are receiving current sensor signals to reduce motor noise. Available analog current inputs are used for range finder or proximity sensor signal 53, first vacuum sensor 54 and auxiliary vacuum sensor 55.

Figure 15:
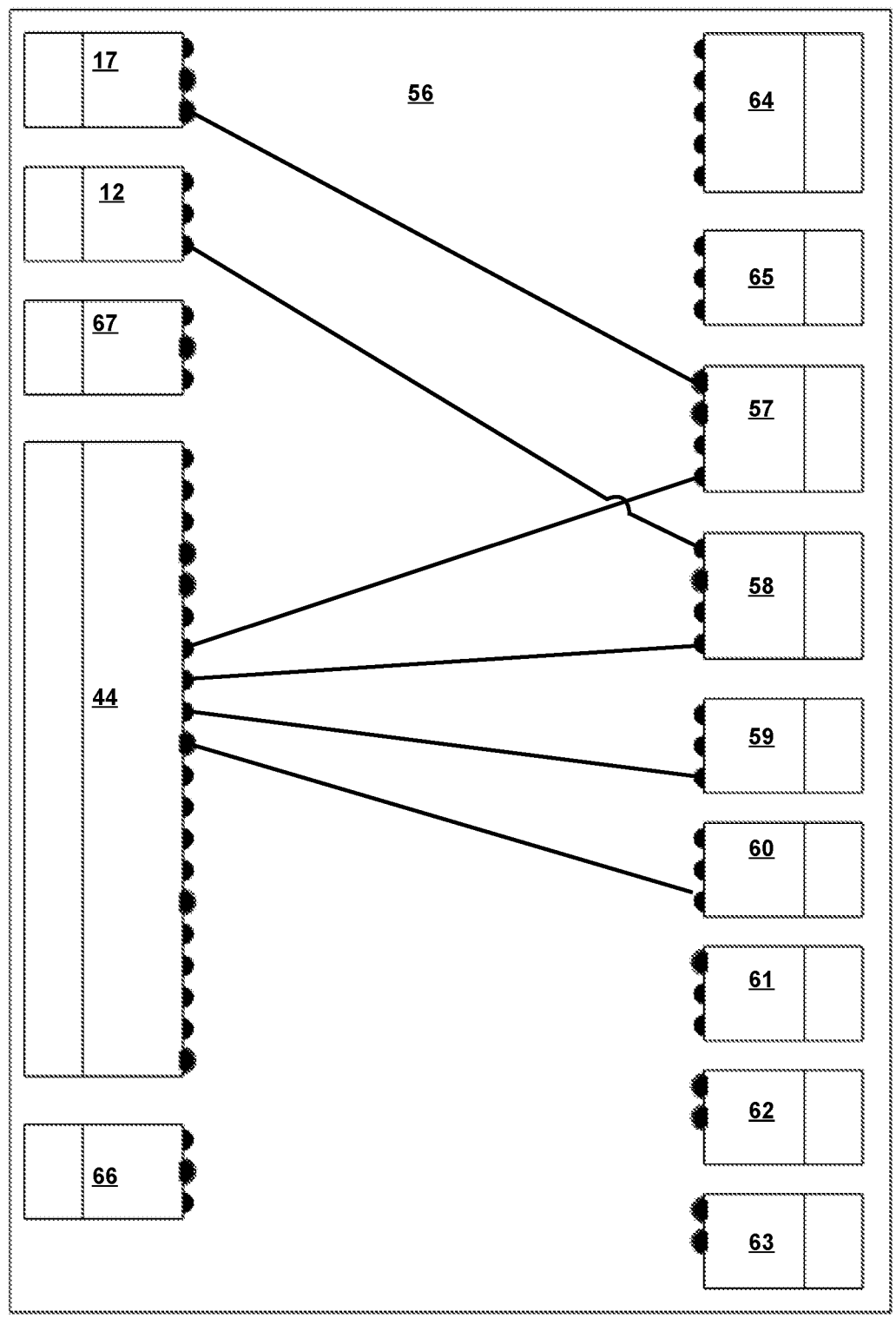
FIG. 15 depicts a component diagram illustrating disposition of component, power and control elements in an example embodiment of the invention.

FIG. 15 depicts a component diagram illustrating disposition of component, power and control elements in an example embodiment of the invention. The diagram is stylized so as to include both wired components and PCB-mounted components.

The wiring harness 44 detailed in the description of FIG. 13 is connected via multi-pin to a printed circuit board (PCB) 56. As detailed above, the wiring harness directs I/O connections from a vibration motor discrete relay 57, a vacuum pump discrete relay 58, a hold solenoid 59, a release solenoid 60, a proximity sensor analog current input 61, a first vacuum sensor analog current input 62 and an auxiliary vacuum sensor analog current input 63. The hold solenoid, release solenoid, proximity sensor, first vacuum sensor analog current input and second vacuum sensor are distinct components connected by wire to the wiring harness.

The vibration motor discrete relay and vacuum pump discrete relay are PCB mounted. Also mounted on PCB are the power supply running 64 on 120 VAC or 240 VAC and providing 24 VDC at 3 amps to the vacuum pump, vibration motor, solenoids and proximity sensor. An ethernet switch 65 for external communications with the control module is mounted to the PCB.

Connected by wire are also the user touchscreen 66 and CPU 67 for the control module. Finally, the vacuum pump 12 and vibration motor 17 are indicated with wired connections to the vacuum pump relay and vibration motor relay, respectively.

Although the present invention has been described in connection with certain specific embodiments for instructional purposes, the present invention is not limited thereto. Accordingly, various modifications, adaptations, and combinations of various features of the described embodiments can be practiced without departing from the scope of the invention.

What is claimed is:

1. A method for at least one of encouraging tissue growth in a user's penis, strengthening male urinary continence, and/or encouraging penile blood flow, wherein the method comprises:
   receiving the user's penis into a vacuum chamber of an apparatus;
   causing a first tensioning interval in the vacuum chamber, the first tensioning interval having a first tensioning interval vacuum parameter and a first tensioning interval duration parameter;
   concurrent with the first tensioning interval, applying a first vibration interval in the vacuum chamber,
   the first vibration interval having a first vibration interval duration parameter, the first vibration interval being applied via a vibration motor having a first vibration interval frequency and a first vibration interval amplitude;
   elapse of the first tensioning interval duration parameter, and
   causing a first recovery interval in the vacuum chamber,
   the first recovery interval having a first recovery interval vacuum parameter and a first recovery interval duration parameter, and
   the first recovery interval vacuum parameter being lower than the first tensioning interval vacuum parameter.

2. The method of claim 1, further comprising the steps of:
   causing a second tensioning interval in the vacuum chamber, the second tensioning interval having a second tensioning interval vacuum parameter and a second tensioning interval duration parameter, the second tensioning interval vacuum parameter being greater than the first tensioning interval vacuum parameter by a first tensioning interval vacuum increase parameter;

concurrent with the second tensioning interval, applying a second vibration interval in the vacuum chamber, the second vibration interval having a second vibration interval duration parameter, the second vibration interval being applied via said vibration motor having a second vibration interval frequency and a second vibration interval amplitude;

elapse of the second tensioning interval duration parameter, and causing a second recovery interval in the vacuum chamber, the second recovery interval having a second recovery interval vacuum parameter and a second recovery interval duration parameter, and the second recovery interval vacuum parameter being lower than the second tensioning interval vacuum parameter.

3. The method of claim 1, further comprising the step of:

setting a value for at least ono a control parameter of the apparatus, the control parameter being taken from a set of control parameters comprising:
said first tensioning interval vacuum parameter;
said first tensioning interval duration parameter;
a first vibration interval frequency parameter;
a first vibration interval amplitude parameter;
said first vibration interval duration parameter;
said first recovery interval vacuum parameter;
said first recovery interval duration parameter,
a second tensioning interval vacuum parameter;
a second tensioning interval duration parameter;
a second vibration interval frequency parameter;
a second vibration interval amplitude parameter;
a second vibration interval duration parameter;
a second recovery interval vacuum parameter;
a second recovery interval duration parameter;
a vacuum increase parameter;
a duration increase parameter;
a duration decrease parameter;
a vibration frequency increase parameter;
a vibration frequency decrease parameter;
a vibration amplitude increase parameter;
a vibration amplitude decrease parameter;
a seal parameter;
a maximum vacuum parameter; and,
a user target vacuum parameter.

4. The method of claim 1, wherein at least one control parameter of the set of control parameters is received from said user.

5. The method of claim 1, further comprising the steps of:

subsequent to elapse of the first vibration interval parameter, using a sensor to make a first determination of user penis length; and recording said first determination of user penis length in a control module of the apparatus, said control module having a persistent, non-volatile memory.

6. The method of claim 1, wherein the vacuum chamber is essentially cylindrical with an exterior diameter and a first interior diameter; and wherein the first interior diameter tapers to a second interior diameter that is smaller than the first interior diameter.

7. The method of claim 1, wherein the first tension interval vacuum parameter is sufficient to cause at least some cells of the user's penis to be stretched to a tensioned or elliptical shape via vacuum tensioning.

8. The method of claim 1, wherein the step of causing a first tensioning interval, in conjunction with the step of applying a first vibration interval, is sufficient to cause micro-tearing of at least some tissue of the user's penis.

9. The method of claim 1, wherein the step of causing a first tensioning interval, in conjunction with the step of applying a first vibration interval and followed by the step of causing a first recovery interval, is sufficient to encourage formation of at least some new cells in the tissue of the user's penis.

10. The method of claim 1, wherein the vacuum parameter of the first tensioning interval, in conjunction with the first vibration interval, is sufficiently high as to induce microtearing in the tissue of the user's penis; and, wherein the vacuum parameter of the first recovery interval is not high enough to induce microtearing in the tissue of the user's penis.

11. The method of claim 1, wherein the vibration amplitude of the first vibration interval has a minimum of approximately 2.1G RMS and has a maximum of approximately 9.2G RMS.

12. A method for at least one of encouraging tissue growth in a user's penis, strengthening male urinary continence, and/or encouraging penile blood flow, wherein the method comprises:

receiving a set of user control parameters from a user to a control module of an apparatus, the set of user control parameters comprising a user target vacuum parameter;

determining a set of apparatus control parameters of the apparatus, the set of apparatus control parameters comprising:

a first tensioning interval vacuum parameter, said first tensioning interval vacuum parameter being lower than said user target vacuum parameter;

a first tensioning interval duration parameter;

a first vibration interval duration parameter;

a first recovery interval vacuum parameter; and, a first recovery interval duration parameter;

receiving a user's penis into a vacuum chamber of said apparatus;

using a vacuum pump of the apparatus to cause a vacuum in the vacuum chamber sufficient to cause an air seal of the vacuum chamber to the body of the user;

using said vacuum pump to cause a first tensioning interval in the vacuum chamber, the first tensioning interval being characterized by the first tensioning interval vacuum parameter and the first tensioning interval duration parameter;

using a vibration motor of the apparatus, applying a first vibration interval according to the first vibration interval duration parameter;

using a sensor, determining a first measurement of length of the user's penis due to said first vibration interval in conjunction with said first tensioning interval;

using the vacuum pump to cause a first recovery interval in the vacuum chamber, the first recovery interval being characterized by the first recovery interval vacuum parameter and the first recovery interval duration parameter, said first recovery interval vacuum parameter being lower than said first tensioning interval vacuum parameter;

using said vacuum pump to cause a second tensioning interval in the vacuum chamber, the second tensioning interval being characterized by said user target vacuum parameter and a second tensioning interval duration parameter;

using the vibration motor of the apparatus, applying a second vibration interval according to a second vibration interval duration parameter; and, using the sensor, determining a second measurement of length of the user's penis due to said second vibration interval in conjunction with said second tensioning interval.

13. The method of claim 12,
wherein the step of causing a first tensioning interval in the vacuum chamber uses a vacuum parameter sufficient to cause at least some cells of the user's penis to be stretched to an elliptical shape via vacuum tension.

14. The method of claim 12,
wherein the step of causing a first tensioning interval in the vacuum chamber uses a vacuum parameter sufficient to cause at least some cells of the user's penis to be stretched to an elliptical shape via vacuum tension; and,
wherein the step of applying a first vibration interval begins after at least some cells of the user's penis are stretched to an elliptical shape via vacuum tension.

15. The method of claim 12,
wherein the step of causing a first tensioning interval in the vacuum chamber uses a vacuum parameter sufficient to cause at least some cells of the user's penis to be stretched to an elliptical shape via vacuum tension;
wherein the step of causing a first tensioning interval, in conjunction with the step of applying a first vibration interval, is sufficient to cause micro-tears in at least some tissue of the user's penis; and,
wherein the step of causing a first tensioning interval, in conjunction with the step of causing a first vibration interval, followed by the step of causing a recovery interval, is sufficient to encourage formation of at least some new cells in the tissue of the user's penis.

16. The method of claim 12,
wherein the step of causing a first tensioning interval, in conjunction with the step of applying a first vibration interval, is sufficient to cause micro-tears in at least some tissue of the user's penis; and,
wherein the vacuum parameter of the first recovery interval is not high enough to induce micro-tearing in the tissue of the user's penis.

17. The method of claim 12, wherein the vacuum chamber is essentially cylindrical with an exterior diameter, a first interior diameter, a user entrance and a closed end; and,
wherein the first interior diameter tapers to a second interior diameter that is smaller than the first interior diameter.

18. The method of claim 12,
wherein the vacuum parameter of the first tensioning interval has a minimum of approximately 20% vacuum and has a maximum of approximately 56.8% vacuum;
wherein the vacuum parameter of the first recovery interval has a minimum of approximately 10% vacuum and has a maximum of approximately 30% vacuum; and,
wherein a vibration amplitude parameter of the first vibration interval has a minimum of approximately 2.1G RMS and has a maximum of approximately 9.2G RMS.

19. The method of claim 12,
further comprising the step of:
receiving a user input;
wherein the vacuum chamber is essentially cylindrical with an exterior diameter, a first interior diameter, a user entrance and a closed end;
wherein the first interior diameter tapers to a second interior diameter that is smaller than the first interior diameter;
wherein the vacuum parameter of the first tensioning interval has a maximum of approximately 56.8% vacuum;
wherein a vibration amplitude parameter of the first vibration interval has a minimum of approximately 2.1G RMS; and,
wherein the step of causing a first tensioning interval, in conjunction with the step of applying a first vibration interval, is sufficient to encourage addition of at least some new cells in the tissue of the user's penis.

20. An apparatus for encouraging at least one of tissue growth in a user's penis, strengthening male urinary continence, and/or penile blood flow, comprising:
a vacuum chamber portion, the vacuum chamber portion being part of an activation module of said apparatus, the vacuum chamber portion having a proximal opening and configured to receive a human penis;
a vacuum pump operatively connected to said vacuum chamber portion;
a vibration motor; and,
a control module, configured to store control parameters and to perform the steps of:
controlling the vacuum pump so as to cause a first tensioning interval in the vacuum chamber portion;
controlling the vibration motor so as to cause a first vibration interval that overlaps with the first tensioning interval;
controlling the vacuum pump so as to cause a first recovery interval;
controlling the vacuum pump so as to cause a second tensioning interval;
controlling the vibration motor so as to cause a second vibration interval that overlaps with the second tensioning interval; and,
controlling the vacuum pump so as to cause a second recovery interval;
the control module moans being configured to receive input via a user interface that is configured to receive user parameters, the user interface being either part of the apparatus or else configured to be part of a separate device that is operatively coupled to the apparatus.

21. The apparatus of claim 20, wherein:
the first tensioning interval has a vacuum parameter and a duration parameter;
the first vibration interval has a vibration frequency parameter, a vibration amplitude parameter and a duration parameter, the first vibration interval duration parameter being less than or equal to the first tensioning interval duration parameter; and,
the first recovery interval has a vacuum parameter and a duration parameter, the first recovery interval vacuum parameter being lower than the first tensioning interval vacuum parameter.

22. The apparatus of claim 20, wherein the control module is configured to store at least one control parameter received from a user via the user interface.

23. The apparatus of claim 20, wherein the control module is configured to store a maximum vacuum parameter that is approximately 56% vacuum or, else, a lower maximum vacuum parameter received via the user interface.

24. The apparatus of claim 20, further comprising:

a sensor inside the vacuum chamber portion, operatively coupled to the control module, wherein said sensor is configured to sense expansion of the user's penis inside the vacuum chamber portion; and, wherein the control module is configured to perform the further steps of:

after the first vibration interval, using said sensor to make a first determination of a user penis length, and recording said first determination as data.

25. The apparatus of claim 20, further comprising:

a pelvic tensioning sensor disposed on or in the activation module, operatively coupled to the control module, wherein said pelvic tensioning sensor is capable of detecting pelvic muscle exercise by the user of the apparatus; and, wherein the control module is configured to perform the further step of:

after the first vibration interval, using said pelvic tensioning sensor to make a first measurement of pelvic muscle exercise by the user of the apparatus.

26. The apparatus of claim 20, further comprising:

a sensor inside the vacuum chamber portion, operatively coupled to the control module, wherein said sensor is configured to sense expansion of the user's penis inside the vacuum chamber portion; and, wherein the control module is configured to perform the further steps of:

during the first tensioning interval, using said sensor to make a first determination that the user's penis is fully tensioned to a first length due to vacuum, and commencing the first vibration interval subsequent to said first determination.

27. The apparatus of claim 20, further comprising:

a sensor inside the vacuum chamber portion, operatively coupled to the control module, wherein said sensor is configured to sense expansion of the user's penis inside the vacuum chamber portion; and, wherein the control module is configured to perform the further steps of:

during the first tensioning interval, using said sensor to make a first determination that the user's penis is fully tensioned to a first length due to vacuum, commencing the first vibration interval subsequent to said first determination;

during the first vibration interval, using said sensor to make a second determination that the penis is fully tensioned to a second length due to vacuum in combination with vibration, and commencing the first recovery interval subsequent to said second determination.

28. The apparatus of claim 20, wherein a vacuum parameter of the second tensioning interval, in conjunction with the second vibration interval, is sufficiently high as to induce microtearing in the tissue of the user's penis; and, wherein a vacuum parameter of the second recovery interval is not high enough to induce microtearing in the tissue of the user's penis.

29. The apparatus of claim 20, wherein the vacuum chamber portion is essentially cylindrical with an exterior diameter, a first interior diameter, and a closed end opposite the proximal opening;

wherein the first interior diameter tapers to a second interior diameter that is smaller than the first interior diameter;

wherein the first interior diameter is nearer the proximal opening;

wherein the second interior diameter is nearer the closed end;

wherein the first tensioning interval has a tensioning interval vacuum parameter;

wherein the first recovery interval has a recovery interval vacuum parameter;

wherein the first vibration interval has a vibration interval amplitude parameter;

wherein the first tensioning interval vacuum parameter has a minimum of approximately 20% vacuum and has a maximum of approximately 56.8% vacuum;

wherein the first recovery interval vacuum parameter has a minimum of approximately 10% vacuum and has a maximum of approximately 30% vacuum; and, wherein the vibration amplitude parameter of the first vibration interval has a minimum of approximately 2.1G RMS and has a maximum of approximately 9.2G RMS.

* * * * *